(12) United States Patent
Biedermann

(10) Patent No.: US 8,930,209 B2
(45) Date of Patent: Jan. 6, 2015

(54) INDIVIDUAL ASSESSMENT AND CLASSIFICATION OF COMPLEX DISEASES BY A DATA-BASED CLINICAL DISEASE PROFILE

(76) Inventor: Barbara Biedermann, Basel (CH)

( * ) Notice: Subject to any disclaimer, the term of this patent is extended or adjusted under 35 U.S.C. 154(b) by 1006 days.

(21) Appl. No.: 12/296,363

(22) PCT Filed: Apr. 5, 2007

(86) PCT No.: PCT/IB2007/000917
§ 371 (c)(1),
(2), (4) Date: Dec. 31, 2008

(87) PCT Pub. No.: WO2007/116295
PCT Pub. Date: Oct. 18, 2007

(65) Prior Publication Data
US 2009/0119337 A1   May 7, 2009

Related U.S. Application Data

(60) Provisional application No. 60/744,460, filed on Apr. 7, 2006.

(51) Int. Cl.
G06Q 10/00 (2012.01)
G06Q 50/00 (2012.01)

(52) U.S. Cl.
USPC .................................................. 705/2; 705/3

(58) Field of Classification Search
USPC ........................................................ 705/2, 3
See application file for complete search history.

(56) References Cited

U.S. PATENT DOCUMENTS

| | | | |
|---|---|---|---|
| 6,369,952 B1 * | 4/2002 | Rallison et al. | 359/630 |
| 7,369,952 B2 * | 5/2008 | Petrich et al. | 702/76 |
| 7,381,819 B2 * | 6/2008 | Min et al. | 536/24.5 |
| 2003/0176931 A1 * | 9/2003 | Pednault et al. | 700/31 |
| 2004/0115735 A1 * | 6/2004 | Yusuf et al. | 435/7.1 |
| 2006/0111849 A1 * | 5/2006 | Schadt et al. | 702/20 |

* cited by examiner

*Primary Examiner* — Neha Patel
(74) *Attorney, Agent, or Firm* — Browdy and Neimark, PLLC

(57) ABSTRACT

An tool and method is disclosed to assess disease activity and to classify complex diseases using basic clinical data. The tools and methods allow identifying and consulting affected individuals based on comprehensive bedside examinations and thus provide a basis for the personalized management of complex diseases.

12 Claims, 11 Drawing Sheets

INDIVIDUAL ASSESSMENT AND CLASSIFICATION OF COMPLEX DISEASES BY A DATA-BASED CLINICAL DISEASE PROFILE

CROSS REFERENCE TO RELATED APPLICATION

This application claims the benefit of U.S. provisional application 60/744,460, filed Apr. 7, 2006, which is incorporated by reference in its entirety.

FIELD OF THE INVENTION

The invention relates to assessment tools, including a systems and/or computer programs and methods for identifying, calculating and indicating a score associated with a disease for an individual or a population based on clinical data such as selected sets of measurable indicator variables and/or parameters obtained by physicians. The tools and methods may be employed to assess the state of one or more diseases in an individual or in a population, in the present and/or in the future,

BACKGROUND OF THE INVENTION

Chronic complex diseases are wide spread and their occurrence has been surging worldwide with an aging and an increasingly sedentary population. One of these complex diseases, namely arteriosclerosis, is a common cause of severe diseases such coronary heart disease (1). To prevent deaths and disabilities, it is important to identify individuals at risk, e.g, in the case of arteriosclerosis, at risk to develop cardiovascular events (2, 3). Several risk factor scoring systems have been developed for this purpose (4, 5). These scoring systems have several limitations (6). First, they contain a temporal and spatial bias: the baseline data from which the score formulas are derived were usually collected in the past, sometimes decades ago, and the individuals participating in the study cohort live in certain regions of the world. Thus, general lifestyle changes within a population which can occur over a short period of time and may have a strong impact on the risk factors for arteriosclerosis (7), are not being considered. Many diseases, including arteriosclerosis, are also affected by the genetic background which varies in populations from different continents (8). Second, most risk score calculations for diseases such as arteriosclerosis end at an age of 65 to 70 years because, e.g., cardiovascular events are highly prevalent in this age group. For this age group, the probability to develop cardiovascular events within the next 10 years is 50%, but drugs used to prevent such events have to be taken infinitely and their side effects are particularly common in the elderly (9, 10). Evidence-based guidelines to treat common disorders such as cardiovascular disease, osteoporosis or diabetes with a multitude of drugs have recently been discussed in the light of the increasing number of patients with more than one of these conditions (11). In order to avoid unnecessary or even harmful multidrug regimens, it is of great importance to allocate treatment precisely to the patients who need it and not to the general population above 70. Third, patients with cardiovascular risk factors (e.g. arterial hypertension, hyperlipidemia or diabetes), e.g., for arteriosclerosis are treated for them: they take antihypertensive, cholesterol or glucose lowering drugs, which all potentially affect the variables entering the prediction algorithm and therefore may influence the estimation of the current risk. Since some of these regimens (e.g. statins or angiotensin converting enzyme inhibitors (12, 13)) have beneficial effects on important pathogenic steps of symptomatic arteriosclerosis and may even revert arteriosclerotic lesions, the question arises whether and particularly when these treatments could be discontinued.

The publications and other materials, including patents, used herein to illustrate the invention and, in particular, to provide additional details respecting the practice are incorporated herein by reference in their entirety. For convenience, the publications are referenced in this text by numerals corresponding to those in the appended bibliography.

Thus, there is a need for accurate assessment of current disease activity for the individual patient to replace or supplement risk prediction tools which are based on probabilities rather than facts. Particularly in view of the fact that complex disease, such as cardiovascular disease, are emerging in less developed countries (14) where accessibility to, e.g., coronary catheterization or other modern vascular imaging facilities is limited, this assessment should preferably be based on data obtained, at least in part, from the patient in a concise, short and affordable examination.

The statistical comparison of more than 70 clinical parameters between patients with proven symptomatic arteriosclerosis and patients without cardiovascular events in the past revealed 25 numerical variables that were different between the two groups. The range of the complete dataset for the symptomatic patients is shown, visually weighed and color coded: lighter gray shading (or green color) represents the quartile closest to the asymptomatic patients, light gray shading (or yellow color) the second, dark gray shading (or orange color) the third quartile and darker gray shading (or red color) the quartile most distant to the asymptomatic patients. This quartile distribution is the basis for the assignment of the individual data-based clinical disease profile and for the calculation of the disease activity score for the individual patient according, in this case, to the following formula: disease activity score=$\Sigma[\alpha_1+\alpha_2+\alpha_3+ \ldots +\alpha_{25}]/(25-[\text{missing variables}])$.

Figure 2:
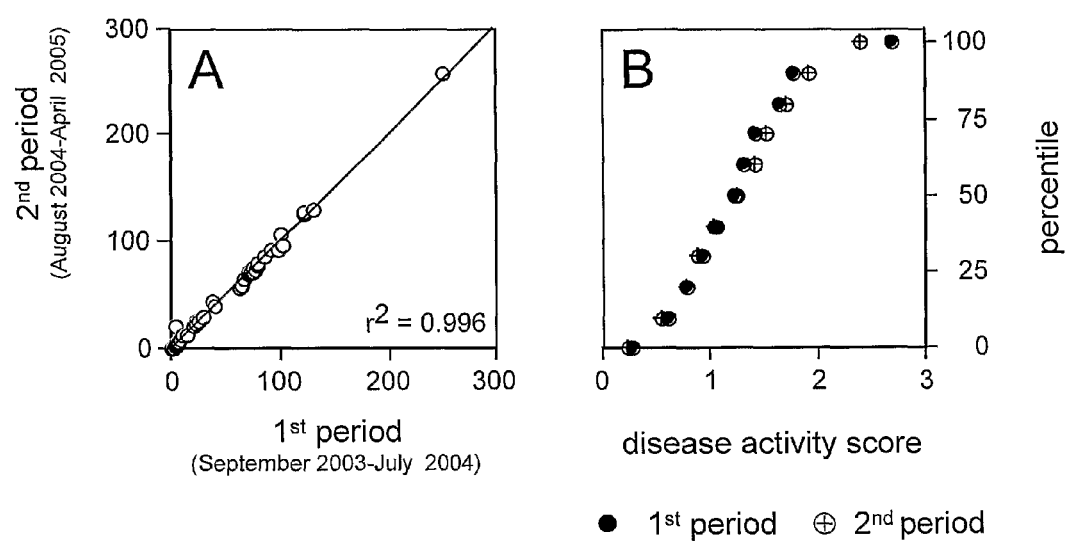

FIG. 2. Reproducibility of the clinical assessment and of the disease activity score.

A. The numerical variables which were collected by different investigators during two different time periods were compared and show an ideal linear correlation. B. The quartile distribution of the disease activity score is nearly identical for the two study periods confirming the consistency and reliability of the method to establish a data-based clinical disease profile.

Figure 3:
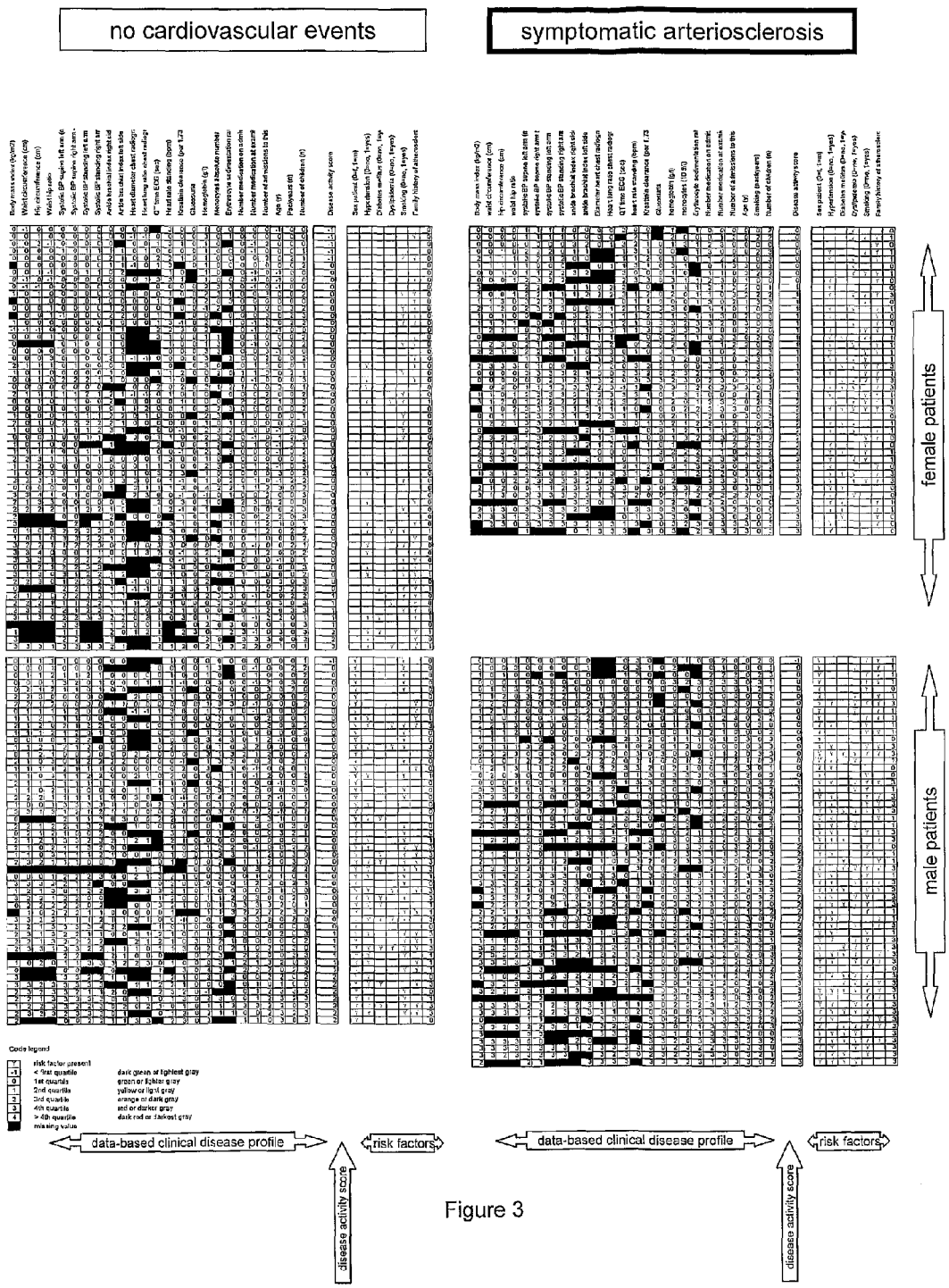

FIG. 3. Alignment of the data-based clinical disease profiles into an array format.

The clinical data arrays are grouped in four quadrants according to the absence or presence of cardiovascular events in the past (left and right panel, respectively) and according to the gender (upper and lower panel, respectively). M=patients with metabolic syndrome. BMI=body mass index. SBP=systolic blood pressure. ABI=ankle brachial index. BSR=blood sedimentation rate.

Figure 4:
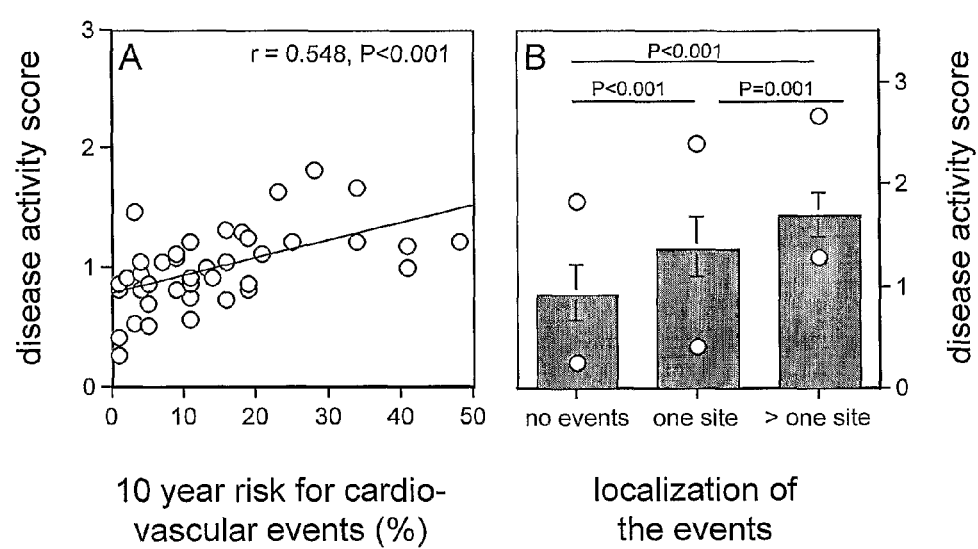

FIG. 4. The disease activity score correlates with prognosis and severity of arteriosclerosis.

A. The 10 year risk to develop cardiovascular events was calculated using the Framingham algorithm (18) and could be shown to be correlated with the disease activity score. B. The disease activity score (median and interquartile range are represented as columns with error bars; maximum and minimum values as circles) are shown for three patients groups: the first including patients without cardiovascular events (n=110), the second including patients with a cardiovascular event at a single site (n=72) and the third including patients with cardiovascular events affecting more than one organ (n=28).

Figure 5:
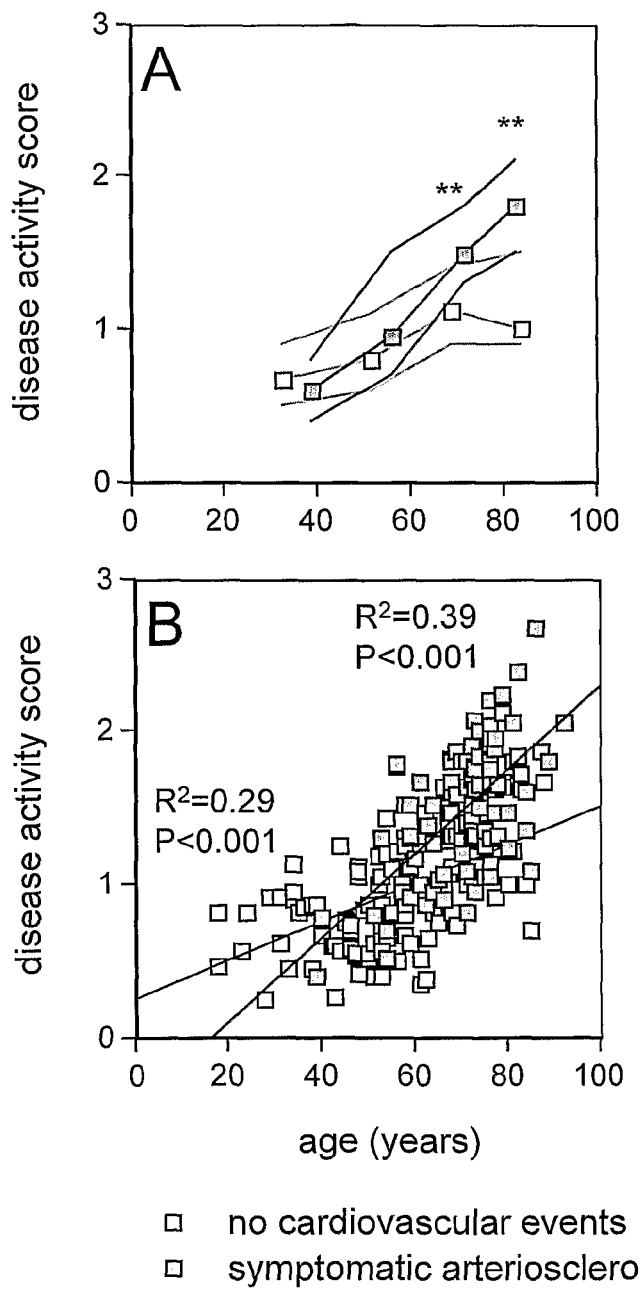

FIG. 5. The disease activity score correlates with age.

Figure 1:
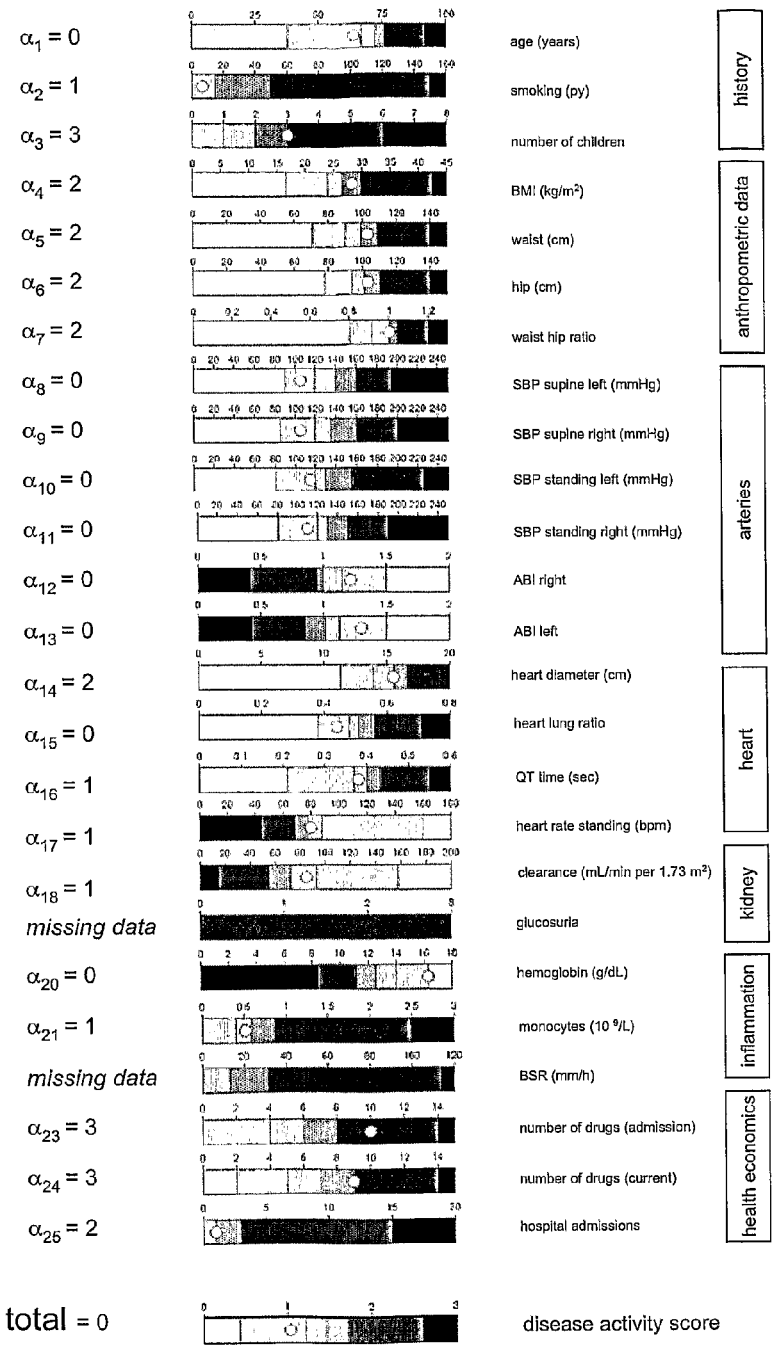
FIG. 1. The Data-based clinical disease profile and the Disease activity score.

FIGS. 6-1 and 6-2. The phenotypical correlation plot of asymptomatic and symptomatic arteriosclerosis.

The 61 clinical datasets for which more than 75% of the data were available were correlated and the linear regression coefficient R calculated. 6-1. Patients without cardiovascular events. 6-2. Patients with symptomatic arteriosclerosis. R-values are shown. If gray scale coded, the figure legend assigns R-values to certain gray scales.

Figure 7:
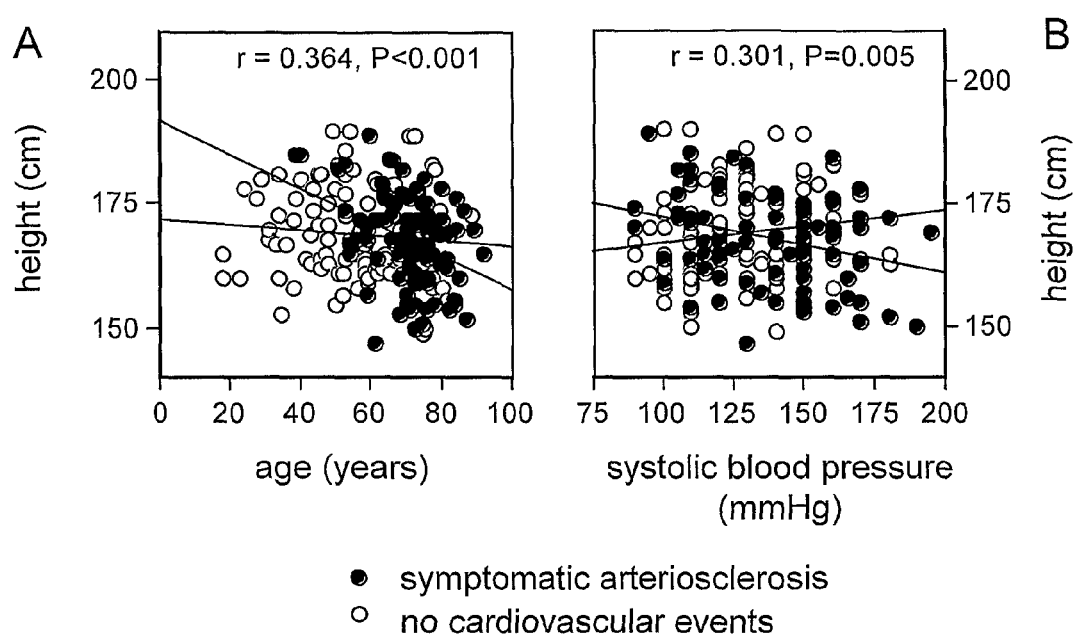

FIG. 7. Symptomatic arteriosclerosis is linked with osteoporosis.

In patients with symptomatic arteriosclerosis but not in patients without cardiovascular events, the body size decreases with age (A) and is negatively correlated with systolic blood pressure (B).

Figure 8:
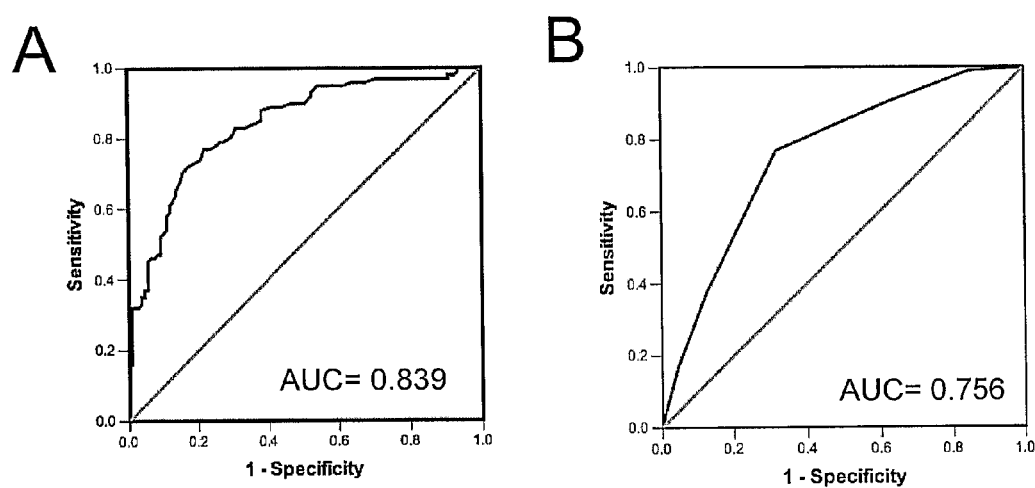

FIG. 8. Receiver operating characteristic (ROC) curve for the disease activity score (A) and the number of risk factors (B). Area under the curve is shown within the graph.

Figure 9:
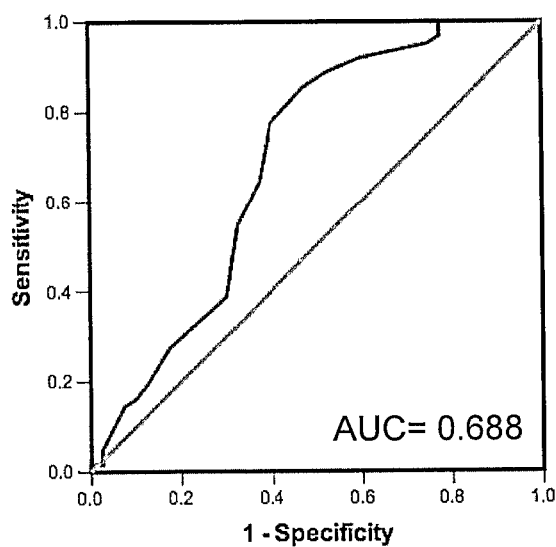

FIG. 9. ROC curve for the Framingham score.

Figure 10:
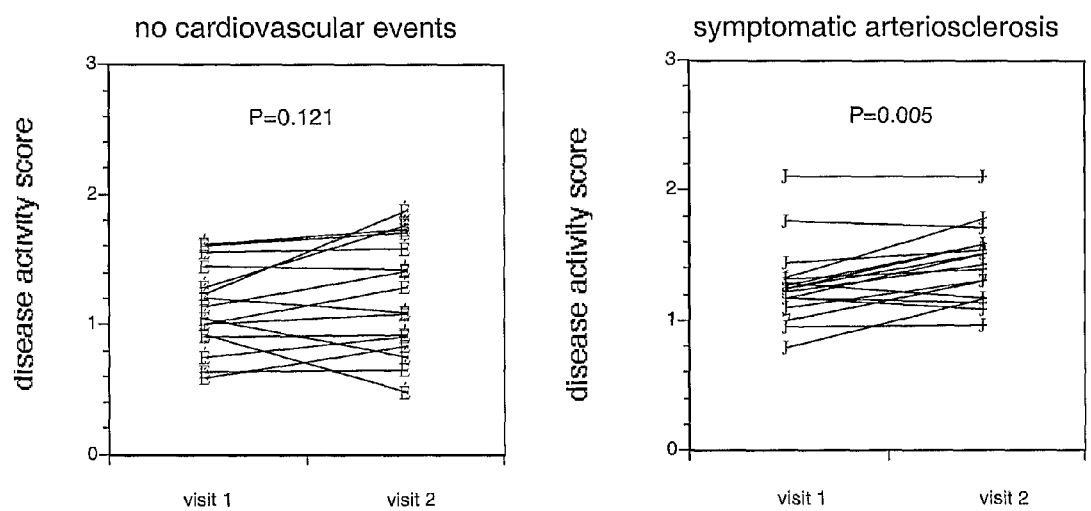

FIG. 10. Comparison of the disease activity score over time for a group of individuals without the disease (left) and a group of individuals with the disease (right).

SUMMARY OF THE INVENTION

The present invention is directed towards an assessment tool for a disease comprising:
(a) a first set of data recorder said first set of data comprising data of measurable indicator parameters and/or variables collected from a first group of individuals having said disease;
(b) a second set of data recorder, said second set of data comprising data of said measurable indicator parameters and/or variables in (a), but collected from a second group of individuals without said disease;
(c) a comparing unit/function which compares said first set of data with said second set of data; and
(d) a selecting unit/function which selects a profiling set from said measurable indicator parameters and/or variables, wherein a coding, such as color, shade or value coding, attributed to each of said measurable parameters and/or variables of said profiling set reflects a disease activity measured by said measurable parameters and/or variables.

Said coding may contribute to a data-based clinical disease profile and/or an activity score of said disease. Said selecting unit/function or a further selecting unit/function may select a correlation set, wherein said coding may correlate at least two different of said measurable indicator parameters and/or variables of the correlation set.

An attribution unit/function may calculate the percentile distribution of each measurable indicator parameter and/or variable of said profiling set of said first and/or second group, wherein said coding reflects this percentile distribution.

The coding may be based on percentile ranges such as, but not limited to, tertile, quartile, quintile, sextile, septile, octile or nonile ranges of said percentile distribution.

The selecting unit/function may select said profiling set from parameters and/or variables having a P-value of less than 0.5, preferably less than 0.4, more preferably less than 0.3, even more preferably less than 0.2, even more preferably less than 0.1, 0.05, 0.025, 0.01, 0.005, 0.0025 or 0.001 in a statistical test comparing two groups such as, but not limited to, the Mann Whitney U test, the student t-test, or the $X^2$ test when compared in (c).

The invention is also directed towards a method for determining measurable parameters and/or variables correlated to a condition and/or disease comprising:
(a) compiling measurable indicator parameters and/or variables;
(b) collecting and/or storing a first set of data for each of said measurable parameters and/or variables collected from a first group of individuals having said disease;
(c) collecting and/or storing a second set of data for each of said measurable parameters and/or variables collected from a second group of individuals without said disease,
wherein said individuals of (b) and (c) are selected from the same population and, optionally, the first and second set of data were collected approximately within the last 5 years, 4 years, 3 years, 2 years, 1 year, 9 months, 6 months, 3 months, 2 months, 1 months, 2 weeks, 1 week, 5 days, 2 days or 24 hours;
(d) selecting a profiling set from said measurable parameters and/or variables; and
(e) optionally, selecting a correlating set from said measurable parameters and/or variables.

The method may further comprise assigning said measurable indicator parameters and/or variables a coding, such as a color, shade or value coding, wherein said coding may reflect a disease activity measured by the measurable parameters and/or variables to the disease and/or condition. The method may also comprise calculating a percentile distribution of each measurable indicator parameter and/or variable of said profiling set and/or correlation set, wherein said coding may reflect this percentile distribution for said first and/or second group. The coding may be based on certain percentile ranges such as, but not limited to, tertile, quartile, quintile sextile, septile, octile or nonile ranges of said percentile distribution.

The invention is also directed towards determining an activity score for at least one condition and/or disease in an individual and/or in a population comprising
measuring the measurable indictor parameters and/or variables of the profiling set in said individual; and
determining the activity score of said disease in said individual or a population from an average of the sum of said coding.

The invention is also directed to uses of any embodiment of the invention.

DETAILED DESCRIPTION OF VARIOUS AND PREFERRED EMBODIMENTS OF THE INVENTION

The article "a" in the context of the present invention means one or more unless otherwise specified.

A disease according to the present invention is any condition that, when manifested in an individual including non-human animals and humans such as patients, can be associated with a set of parameters and/or variables that are measurable and are indicative of said condition or disease (hereinafter "measurable indicator parameters and/or variables"). Variables are numerical, while parameters comprise non-numerical clinical data. (see, "Sapira's Art & Science of bedside diagnosis". Second Edition, Jane M. Orient. Lippincott Williams & Wilkins. 2000). In a preferred embodiment the disease is a common, complex condition or diseases for which a clear clinical definition exists, such as, but not limited to, a definition provided by the World Health Organization (WHO). An individual is said to have a disease if the individual could be diagnosed with the disease according to such a clear clinical definition. An individual I said to be without a disease if either his/her history or an examination does not indicate that the individual has the disease.

A disease activity according to the present invention is a quantifiable measurement of disease ranging from no disease activity (=0) to maximal disease activity (=m, wherein m is the maximum activity value assigned to a disease).

An assessment tool according to the present invention is any system, e.g., a computer system, or an array of functions, such as a computer program, which is associated with a physical structure such as, but not limited to, a server, a CD, DVD or similar. The tool may be made available to clients, such as, but not limited to, hospitals, teleconsultants or the end user, via the internet. In a preferred embodiment, the assessment tool and methods of the invention allow for consideration of environmental changes that occur or have occurred, e.g., in a population in the assessment of a disease. This means, the assessment may be performed based on data that was collected proximate to its use and/or within the relevant population. Thus, in a preferred embodiment of the invention, the data for a standard reference, is collected within the time frame of less than two years, less than one year, less than six month, less than 3 month, or less than one month or even less than a fortnight from its use, e.g., as part of the assessment tool of the present invention. Accordingly, the standard reference might stem from a contemporary cohort of, e.g., individuals with or without the disease or set of diseases in question.

A recorder is, in the context of the present invention any collecting and/or storing unit or function. A recorder may collect and/or stores a sets of data (a set of data recorder), such as measurable indicator parameters and/or variables, pertaining to, e.g., a particular disease or a variety of diseases. In a preferred embodiment, the recorder stores measurable indicator parameters and/or variables that have been collected from individuals. As the person skilled in the art will appreciate, a wide variety of options exists how data such as such a set of data can be collected and stored all of which form part of the present invention. In one embodiment, the recorder is a central processing unit of a PC or a server. The recorder can also take the form of a function that is associated with, including embedded in, a physical structure such as, but not limited to, a CD, DVD or other, e.g., storing device. The term unit/function, e.g. a selecting or comparing unit/function, similarly indicates that selecting and/or comparing can be taken over by a distinct physical entity, but can also just be a function associated with a distinct physical structure such as, but not limited to, a CD, DVD or other, e.g., storing device. The measurable indicator parameters and/or variables are preferably readily assessable ones, e.g., via bedside examination and/or a number of laboratory tests. Thus, they can be assessed in facilities lacking sophisticated equipment, such as expensive imaging equipment. For example, the indicator parameters and/or variables may be assessed in a mobile or temporary facility. As the person skilled in the art will appreciate, the measurable indicator parameters and/or variables vary to different degrees from disease to disease. The questionnaire in Appendix I as well as the Table in Appendix II provide convenient tools to ascertain these parameters and/or variables for a wide variety of diseases. However, it is well within the skill of the artisan to modify a questionnaire and/or table of this kind. Also, it might be desirable to adjust such a questionnaire and/or table to take into consideration the specifics of, e.g., a population, location or time in which/where/when the assessment is performed.

A profiling set is a collection of measurable indicator parameters and/or variables from a relevant number of individuals that forms the basis to profile a certain disease, e.g., arteriosclerosis. A profiling set will comprise at least a majority (more than 50%) of measurable indicator parameters and/or variables that can be clearly linked to a particular disease, e.g. by establishing statistically significant differences between individuals having a disease and individuals without the disease and selecting those that showed such differences between the two groups. Thus, in a preferred embodiment of the invention, the profiling set comprises, consists of or essentially consists of a set of parameters and/or variables having a P-value of less than 0.5, preferably less than 0.4, more preferably less than 0.3, even more preferably less than 0.2, even more preferably less than 0.1, 0.05, 0.025, 0.01, 0.005, 0.0025 or 0.001 in a statistical test comparing two groups such as, but not limited to, the Mann Whitney U test, the student t-test, or the $X^2$ test, wherein this set is a subset of parameters/variables selected after comparing parameters/variables of a first group of individuals having the disease and a second group not having the disease.

A data-based clinical disease profile according to the present invention profiles a disease in an individual employing a profiling set. It comprises, consists of or essentially consists of measurable indicator parameters and/or variables that have been attributed a coding which relates the value measured for this parameters and/or variables to a reference value, such as the average value measured for this parameter and/or variable in a relevant number of individuals having the disease or, alternatively, in a relevant number of individuals not having the disease. These groups of individuals are also referred to herein as reference or standard reference. In one embodiment the reference consists of or consists essentially of individuals having the disease.

A disease activity score according to the present invention is an average of the measurable indicator parameters and/or variables of a data-based clinical disease profile. It can thus provide a single measurement for an individual's disease activity. In certain embodiment, the disease activity score obtained from individuals of a population is averaged to obtain a disease activity score for such a population or for specific segments thereof. For example, the population may be individuals treated in a particular clinic and the specific segments may be male or female patients or patients above or below a certain age. In certain embodiment of the invention, the disease activity may also be assessed via a simple summation of the measurable parameters and/or variables.

A correlation set is a collection of measurable indicator parameters and/or variables from a relevant number of individuals that forms the basis to correlate members of said collection to each other and/or to a certain disease, e.g., arteriosclerosis, e.g., via a phenotypical correlation plot. "Correlating" or "to correlate" in this context means establishing a link between, e.g., two variables, irrespective of whether or not statistically significant. The data set of the correlation set is broader of a profiling set an thus allows correlating, that is making a connection between of measurable indicator parameters and/or variables between a connection has previously not or not clearly been determined.

A population according to the present invention is a group of individuals that stem from the same geographical area, which may be a continent, a country, a state, a city, a town, a district or a building such as a hospital or a clinic. In a preferred embodiment of the present invention, the profiling set and/or correlation set is drawn from individuals from one population. The tools and or methods of the present invention are, in a preferred embodiment, tied to such a population or a subset thereof. This allows personalized and targeted treatment of patients with complex diseases or with a risk to develop them. The invention also allows to determine trends of a disease within a population.

The invention is, in a preferred embodiment, directed at a comprehensive clinical data array that describes a common, complex human disease such as symptomatic arteriosclerosis. In one embodiment, the invention is directed at accurately determining the individual patient's disease activity using a set of non-invasive, affordable and accessible clinical tests. In a particularly preferred embodiment of the invention, the patient's data is compared with a contemporary cohort of patients suffering from the disease (i.e. symptomatic arteriosclerosis), a feature classical cardiovascular risk calculation tools generally do not have. The patients who serve as an internal reference group, are, e.g., living in the same area and they are treated at the same institution. Thus, they are drawn form the same population. This circumstance avoids the temporal and spatial bias that may affect the accurate disease prediction by most known risk algorithms (6).

Facing the diagnostic break-through of modern imaging technologies in the late $20^{th}$ century, clinical examination is becoming an orphan science among clinicians and particularly among young physicians. In the following, data-based clinical disease profiles, will be discussed using symptomatic arteriosclerosis as a non-limiting example. The data-based clinical disease profile, is, in this embodiment, entirely based on simple clinical findings such as patient's history, bedside procedures and a few lab tests. Its strength lies in the detection of the individual disease activity both for asymptomatic patients without treatment but also for patients with fully established secondary prevention. This individualized assessment forms the basis for the personalized treatment of arteriosclerosis. It facilitates focused treatment of the system which is most involved in (such as body shape or general inflammation) or most affected by (such as arteries, the heart or the kidney) the disease.

In one preferred embodiment of the invention, the positive predictive value of the disease activity score is assessed. For asymptomatic patients this score correlates with the 10-year risk to develop cardiovascular events as calculated by the Framingham algorithm (18), thus suggesting its prognostic significance. Accordingly, in a preferred embodiment of the present invention the disease activity score of an individual without the respective disease, is used prognostically forecasting a disease development and/or onset for about 15 years, about 10 years, about 5, years, about 4 years, about 3, years or about 2 years. The data-based clinical disease profile and the disease activity score is, in a preferred embodiment, defined by the same cohort of patients for which it sets the reference, that is, its data is drawn from the same population as, e.g., the assessed individual. Notably, both single numerical variables and the disease activity score have been shown reproducible when collected by different investigators during different time periods. The fact that the disease activity score increases with the severity of arteriosclerosis as assessed by the number of organ beds affected by the disease reflects a biologically relevant assessment. Third, age is an important risk factor for cardiovascular events (26) and, not surprisingly, age also affects the disease activity score. Patients with symptomatic arteriosclerosis show an accelerated progression of arteriosclerosis as measured with the disease activity score that is revealed after age forty. Although the disease activity score is significantly higher for symptomatic patients, there is significant overlap with asymptomatic individuals. Additional, comprehensive diagnostic tools such as genomic or transcriptomic tests can, in certain embodiment, be employed to separate the two patient groups, but also to identify presymptomatic individuals accurately. Finally, the conditions that precipitate the development of symptomatic arteriosclerosis are evolving with time. They may be different in various regions of the world and are subject to the medical management, be it primary or secondary prevention strategies or access to revascularization procedures. Therefore, this data-based clinical disease profile may look different 10 or 20 years from now, it may look different in the setting of a private practice or in a tertiary care referral center of a university hospital.

As the person skilled in the art will appreciate, the present approach of assessing a complex disease with bedside, accessible and affordable clinical tests can be adopted for other common conditions such as chronic obstructive pulmonary disease, osteoporosis, even cancer or other conditions as those described elsewhere herein. The comprehensive, unbiased collection of clinical datasets together with an unambiguous assignment of the diagnostic vignette allows to confirm or discover linked conditions such as osteoporosis which seems to accompany symptomatic, but not asymptomatic arteriosclerosis.

The invention will be explained in the following using symptomatic arteriosclerosis as a non-limiting example.

In the context of this example, it was tested whether non-invasive, bedside diagnostic procedures and a set of additional, simple tests that are usually part of the initial evaluation of a patient are able to identify individuals with symptomatic arteriosclerosis. In a prospective observational clinical cohort study data was collected that were obtained by a physician in a standardized clinical exam. A set of more than 70 numerical variables were systematically compared between patients who suffered from symptomatic arteriosclerosis and patients who had no cardiovascular events in the past. 25 of these datasets were clearly different between the two patient groups. The quartile distribution of these data was the basis of a quantitative scoring system which formed the basis for a color coded, data-based clinical disease profile of arteriosclerosis. This comprehensive clinical approach to describe a complex disease such as symptomatic arteriosclerosis may be the first step to evaluate personalized, targeted treatment strategies for individual patients.

Methods

Patient Recruitment 718 in-patients who were treated for any reason at one single ward of a department of a Hospital, were screened for exclusion criteria to participate in the study. Exclusion criteria that were fulfilled by 40% of the patients were either the inability to give informed consent or terminal illness. Two physicians (C. S., M. M.) were sequentially involved in the data collection that covered two study periods: period 1: 11 months (C. S.), and period 2: 8 months (M. M.). Overall, 431 patients without exclusion criteria were personally confronted with the study protocol. 269 patients consented to participate. The patients were grouped in three categories based on the clinical history: group 1—no cardiovascular events in the past; group 2—cardiovascular events in the past which define symptomatic arteriosclerosis; group 3—symptoms were compatible with symptomatic arteriosclerosis, but clinical evidence to prove it was lacking. For the data-based clinical disease profile, patients without cardiovascular events (group 1) and patients with proven, symptomatic arteriosclerosis (group 2) were compared (Table 1). Cardiovascular events which defined symptomatic arteriosclerosis in this patient cohort were a) for coronary heart disease: myocardial infarction, significant stenosis of coronary arteries as assessed by angiography, angina pectoris with signs of myocardial ischemia, history of coronary bypass surgery or other revascularization procedures, b) for cerebrovascular disease: ischemic stroke, history of carotid surgery, c) for peripheral arterial occlusive disease: ankle brachial index <0.9 (15) and symptoms of claudicatio intermittens, significant stenosis of arteries and symptoms of claudicatio, history of peripheral bypass surgery or other revascularization procedure, d) for aortic arteriosclerosis: symptomatic aortic aneurysm, infrarenal diameter >3 cm (16) and e) for arteriosclerosis of the kidney: renal artery stenosis, impaired renal function (17) with normal urine analysis, history of renal artery revascularization procedures. Male sex, arterial hypertension, diabetes mellitus, dyslipidemia, smoking and a positive family history for cardiovascular disease were the six conventional cardiovascular risk factors which were assessed based on the clinical history (18).

Comprehensive Clinical Assessment

All participants were subject to a standardized interview (H, history) and examined in a standardized clinical examination (C) (see Appendix I for questionaire). The clinical examination started with the patient in the standing position. Body weight and size, waist and hip circumference, blood pressure and heart rate were measured on both arms in the standing position first. Thereafter, the examination was continued in the supine position. Blood pressure and heart rate measured in supine position were usually obtained at the end of the examination, together with the determination of the ankle brachial index (ABI). It was assessed using bedside doppler ultrasound (Dopplex 5 MHz, HNE Healthcare GmbH, Hilden, Germany). Patients with incompressible leg arteries had a formal ABI of more than 1.5 and these excessively high indexes were excluded from the dataset. The patient's record served as a source for additional information such as laboratory tests (L), X-rays (X), electrocardiogram (E), stress test or echocardiogram. For this aspect, it was a purely observational study. No additional laboratory testing were performed except what was requested by the treating physicians. From the full clinical assessment which was collected in an electronic data base, 76 numeric variables were selected (see Supplemental Table 1) for further statistical analysis. 15 (20%) were obtained from the interview, 19 (25%) from the clinical examination, 33 (43%) from the laboratory tests and 9 (12%) from x-ray, electrocardiogram, stress test or echocardiogram. For 15 of these 76 parameters, the dataset was incomplete, i.e. information from less than 75% of the patients were collected (Appendix II).

Data-Based Clinical Disease Profile and Disease Activity Score

For 61 of the 76 numeric variables, data were available for more than 75% of the patients. These datasets were compared between patients without cardiovascular events in the past (group 1) and patients with proven symptomatic arteriosclerosis (group 2) using the Mann Whitney U test (Appendix II). For 25 variables (41%), the P-value was below 0.1 and these parameters were selected to be part of the data-based clinical disease profile (Table 2). For both groups, the percentile distribution of the data was calculated and the quartile ranges are shown (Table 2). The group of patients with the disease, i.e. with proven symptomatic arteriosclerosis (group 2, n=100 patients) was defining the standard reference for the data-based clinical disease profile. The calculated quartile ranges served for color coding the patient's individual data (Table 2 and FIG. 1). For most of the numerical variables, patients with symptomatic arteriosclerosis had higher median values than the patients without cardiovascular events. Therefore, lighter gray shading (or green color) was assigned to the lowest quartile closest to the asymptomatic patients, light gray shading (or yellow color) to the second, dark gray shading (or orange color) to the third quartile and darker gray shading (or red color) to the quartile most distant to the asymptomatic patients. Values below the minimal value were coded as lightest gray and values above the maximal value were coded as darkest gray. Exceptions to this rule were the ankle brachial index, the peripheral heart rate at standing position, the creatinine clearance and the hemoglobin concentration. For these 5 parameters, the patients with symptomatic arteriosclerosis had lower median values compared to the asymptomatic patients, and therefore color coding followed the opposite rule: the highest quartile range was assigned to the lighter gray shading (or green color), the 3rd to the light gray shading (or yellow color), the $2^{nd}$ to the dark gray shading (or orange color) and the lowest quartile range to the darker gray shading (or red color) (FIG. 1).

The Phenotypical Correlation Plot

Correlation profiling is used by physiologists to assess the influence of genotype on cardiovascular phenotype (19, 20). In a similar way, we used this approach to comprehensively compare the phenotype of patients with symptomatic arteriosclerosis and patients without cardiovascular events (FIG. 6). The 61 parameters, for which a complete dataset was available, were correlated linearly with each other and the linear correlation coefficient R was calculated. Again, color coding was applied to visualize different and opposite degrees of correlation (FIG. 6-1, 6-2, legend). Correlation coefficients of 0+/−0.01 are shown in black, increasingly positive correlations are turning into gray and light gray, whereas increasingly negative correlations are turning into light scattered and strong scattered.

Statistical Analysis

All statistical analyses were performed using SPSS version 12.0 (SPSS Inc., Chicago Ill., USA). The numeric data which were obtained in the group of patients with symptomatic arteriosclerosis were compared to the patients without cardiovascular events using the Mann-Whitney U test. The presence or absence of cardiovascular risk factors was compared between the two groups using the $X^2$-test. Linear correlation coefficients were determined by the least squares method and correlations were tested for significance using the Spearman's test. P-values <0.05 were supposed to indicate a significant difference between the groups.

Receiver Operating Characteristic (Roc) Curve for the Assessment of Diagnostic Suitability of the Disease Activity Score The disease activity score for arteriosclerosis was analyzed and compared to a number of conventional risk factors as well as to the Framingham score as used as diagnostic tool for arteriosclerosis.

Evolution of the Disease Activity Score

The prospective evolution of the disease activity score depending on the state of the disease was assessed by determining the disease activity score in a individual in a two year interval.

Results

The Clinical Bedside Examination Identified Patients with Symptomatic Arteriosclerosis Of the 269 patients who participated in this study, 100 (37%) had symptomatic arteriosclerosis, i.e. they had suffered from cardiovascular events in the past. 110 (41%) had no history of cardiovascular events such as myocardial infarction, stroke, intermittent claudication, revascularization procedures or other disease defining conditions (Table 1). For 59 (22%) patients, the definite allocation to one of these two groups was not possible. The characteristics of the patients without cardiovascular events in the past and of the patients with proven symptomatic arteriosclerosis are summarized in Table 1. On average, patients with symptomatic arteriosclerosis were older, and all conventional risk factors were significantly more common in this group. Smoking, a positive family history of cardiovascular events and arterial hypertension were the most prevalent risk factors for both patient groups (Table 1). 60% of the patients with symptomatic arteriosclerosis had coronary heart disease, 26% had cerebrovascular disease, 26% peripheral arterial occlusive disease, 7% aortic and 7% renal arteriosclerosis. For about a quarter of these patients, more than one vascular bed was affected by the disease.

For 15 of the 76 numerical variables tested, the dataset was incomplete (Appendix II) and they were therefore excluded from the further statistical analysis. Of the remaining 61 parameters, 25 (43%) showed a consistent difference (P-value <0.1 in the Mann-Whitney U test) when they were compared between the two patient groups. The majority was obtained in the bedside examination: 7 (28%) from the interview, 11 (44%) from the clinical examination, only 5 (20%) from laboratory tests and 3 (12%) from chest X-ray or electrocardiogram. For these 25 variables, the quartile distribution was calculated (Table 2) and the normalized interquartile limits are shown as color coded columns in FIG. 1. These interquartile limits define the range for color coding of the individual patient's data: depending on the value for age, number of pack years, number of children etc which are displayed as a white circle (FIG. 1), either green, yellow, orange or red color is assigned to the variable. The color coded values obtained for the 25 variables are then used for the calculation of the disease activity score: a green value adds 0, a yellow value 1, an orange value 2 and a red value 3 points. The sum is divided by the total number of variables assessed which is ideally 25 (FIG. 1). Therefore, the scale for the score ranges from a minimal value of 0 to a maximal value of 3. Each of the 25 variables contributes one $25^{th}$ part of the score value. Accordingly, in this example, the formula to calculate the disease activity score is $\Sigma[\alpha_1+\alpha_2+\alpha_3+\ldots+\alpha_{25}]/$ (25-[missing variables].

Reproducibility of the Data-Based Clinical Disease Profile

Since 18 of the 25 variables which contributed to the disease activity score were obtained by a physician during the clinical examination and therefore could be subject to inter-observer variability, it was tested whether two independent observers would obtain similar results during two consecutive study periods. During the first period lasting 11 months and during the second period, lasting 8 months, the median values for the 75 numeric variables showed on average excellent correlation (FIG. 2A). When the variables were compared during the two study periods using non-parametric tests, only four parameters showed a significant difference in the group of symptomatic patients: the hemoglobin concentration, the monocyte count and the waist and hip circumference (Appendix III). In contrast, for the patients who did not suffer from cardiovascular events, 16 variables were different between the two study periods. This suggests that a more heterogeneous collection of diseases in this second group could explain the more pronounced diversity of clinical findings. This observation gives additional support for choosing the symptomatic patients to set the reference for the data-based clinical disease profile and for the disease activity score. The percentile distribution of the disease activity score was also calculated between the two study periods (FIG. 2B). It showed a reproducible, normal distribution when it was obtained from different patients and by different investigators.

The Data-Based Clinical Disease Profile: a Rational Basis for the Individual Assessment and Classification of Arteriosclerosis Most of the 25 variables which were significantly different in this systematic and comprehensive comparison of clinical information from symptomatic and asymptomatic patients reflect important clinical signs of arteriosclerosis: the anthropometric data reveal abdominal obesity (21), the elevated systolic blood pressure (22) and the reduced ankle brachial index (15) are the consequence of reduced wall compliance and stenotic arteries, cardiomegaly identifies left ventricular hypertrophy (23), QT prolongation may correlate with electric vulnerability (3), diminished creatinin clearance and glucosuria reflect kidney injury (17). Anemia, monocytosis and elevated blood sedimentation rate are signs of chronic inflammation (24) and finally, the high number of drugs and repetitive hospitalizations are health economic aspects of symptomatic arteriosclerosis (FIG. 1). These categories which emerged from the data analysis have immediate implications for the individual classification of the disease. For example, the male patient whose data are shown in FIG. 1 (white circles) had a myocardial infarction three years ago. His disease profile is drawing the physician's attention to abdominal obesity as the only remaining, clinically apparent sign of the disease under combined anti-hypertensive and lipid lowering treatment.

When the color coded disease profiles obtained from each individual patient are aligned in an array format (FIG. 3) the patient cohort can be divided into the following four groups: female patients without cardiovascular events (upper left quadrant), female patients with symptomatic arteriosclerosis (upper right quadrant), male patients without cardiovascular events (lower left quadrant) and male patients with symptomatic arteriosclerosis (lower right quadrant). Within the quadrants, the data-based clinical disease profile is shown first and it is followed by the disease activity score. The conventional risk factors identified by gray boxes are shown next, and the sum of risk factors which are normalized to the symptomatic patients are shown in a color coded, visually weighed manner. Within each of the four groups, the patients are sorted according to their disease activity score. For the asymptomatic patients, this sorting strategy reveals a cluster of both female and male patients with the metabolic syndrome (FIG. 2, brackets): they have abdominal obesity, elevated systolic blood pressure and often diabetes (25). For the symptomatic patients shown on the right panel, this clustering of the metabolic syndrome is less evident. However, the array of the symptomatic patients reveals a gender-specific, distinct profile of the disease: whereas the female patients, despite of taking the same number of drugs, have on average higher, uncontrolled systolic blood pressure (145 (125-160) mmHg versus 130 (115-148) mmHg, P=0.02) the male patients are rather obese having a higher body mass index (27.7 (24.6-30.7) kg/m² versus 25.4 (23.3-28.1) kg/m², P=0.04 and a higher waist hip ratio (1.02 (1.0-1.07) versus 0.91 (0.88-0.97), P<0.001) than female patients.

The Data-Based Disease Activity Score Correlates with the 10-Year Risk for Cardiovascular Events, with the Severity of the Disease and with Age.

For 40 of the 110 patients without cardiovascular events the dataset was complete to calculate the Framingham risk score (ref). This was translated into the 10-year risk to suffer from cardiovascular events. This 10-year risk showed a weak but significant correlation with the disease activity score (FIG. 4A). Furthermore, patients with extensive arteriosclerosis which affects more than one vascular bed had a significantly higher disease activity score than patients who had only one organ involved or patients without cardiovascular events in the past (FIG. 4B). Finally, the disease activity score is significantly correlated with age for both asymptomatic and symptomatic patients (FIG. 5). However, the rate of progression of the disease with time as identified by the linear curve fit of the disease score with the patient's age is faster in symptomatic patients (FIG. 5). For the patients older than 70 years, the disease activity score was significant higher in the symptomatic than in the asymptomatic group (1.65 (1.33-1.84) versus 1.23 (1.05-1.53), P<0.001).

The Phenotypical Correlation Plot is a Tool to Identify Other Conditions Linked with Symptomatic Arteriosclerosis.

The phenotypical correlation plots for the asymptomatic (FIG. 6A) and symptomatic (FIG. 6B) patients reveal a good association between the anthropometric data and the blood pressure measurements, for both groups of patients. Within the symptomatic patients, body height was negatively correlated with age and with all the four systolic blood pressure measurements (FIG. 6B, insert, arrows) whereas in patients without cardiovascular events, there was no obvious or consistently negative correlation observed. This unexpected finding could be translated into the concept (FIG. 7) that symptomatic arteriosclerosis is linked with osteoporosis (as measured by an age dependent decrease in body size), and that for an individual patient with symptomatic arteriosclerosis, a smaller size is linked to stiffening and loss of compliance of the arterial wall (as measured by an elevated systolic blood pressure).

The Receiver Operating Characteristic (ROC) Curve for the Assessment Shows that The Disease Activity Score is Highly Suitable for the Assessment of Disease Activity As can be seen from FIGS. 8 and 9, the area under the curve is 0.688 for the Framingham score, 0.756 for the number of risk factors in the individuals and 0.839 for the disease activity score.

The Disease Activity Score Increases Significantly Over Time in Individuals with the Disease but not in Individuals without the Disease It was tested how the disease activity score evolves prospectively in patients suffering from symptomatic arteriosclerosis compared to individuals free of cardiovascular events.

It was demonstrate that within two years, the disease activity scores increases significantly in patients with symptomatic arteriosclerosis but not in individuals without active disease FIG. 10. The significance test used to determine the difference between disease activity score during visit 1 and visit 2 was the Wilcoxon test.

TABLE 1

| Patient characteristics | | | |
|---|---|---|---|
| | No cardiovascular events (n = 110) | Symptomatic arteriosclerosis (n = 100) | P-values[#] |
| Cardiovascular risk factors n (%) | | | |
| Male sex | 51 (46.4) | 57 (57) | 0.095 |
| Age (years) | 56.00 | 72.00 | <0.001 |
| Body mass index (kg/M$^2$) | 25.6 | 26.40 | 0.085 |
| Arterial hypertension | 40 (36.4) | 67 (67) | <0.001 |
| Diabetes mellitus | 12 (10.9) | 30 (30) | 0.005 |
| Dyslipidemia | 9 (8.2) | 50 (50) | <0.001 |
| Smoking | 57 (51.8) | 61 (61) | 0.017 |
| Family history of cardiovascular disease | 48 (43.6) | 61 (61) | 0.038 |
| Drugs at examination n (%) | | | |
| Antiplatetelet drugs | 7 (6.4) | 69 (69) | <0.001 |
| Anticoagulants | 27 (24.6) | 36 (36) | 0.07 |
| Nitrates | 1 (0.9) | 18 (18) | <0.001 |
| Betablockers | 19 (17.3) | 60 (60) | <0.001 |
| Diuretics | 17 (15.5) | 48 (48) | <0.001 |
| ACE inhibitors | 14 (12.7) | 56 (56) | <0.001 |
| Angiotensin II receptor blockers | 8 (7.3) | 11 (11) | 0.347 |
| Ca$^{2+}$ channel blockers | 7 (6.4) | 26 (26) | <0.001 |
| Oral glucose-lowering agents | 9 (8.2) | 14 (14) | 0.178 |
| Insulin | 5 (4.6) | 21 (21) | <0.001 |
| Statins | 14 (12.7) | 68 (68) | <0.001 |
| Other drugs | 5 (4.6) | 8 (8) | 0.299 |
| Cardiovascular events defining symptomatic arteriosclerosis % | | | |
| Coronary heart disease | — | 60 | |
| Myocardial infarction | — | 49 | |
| Significant stenosis of coronary arteries (angiographic findings) | — | 23 | |
| Angina pectoris with signs of myocardial ischemia (e.g. exercise testing) | — | 9 | |
| History of revascularization | — | 14 | |
| Cerebrovascular disease | — | 26 | |
| Ischemic stroke | — | 26 | |
| Peripheral arterial occlusive disease | — | 27 | |
| Ankle-brachial-index < 0.9 and symptoms of claudicatio intermittens | — | 14 | |
| Angiographically proven and symptoms of claudicatio intermittens | — | 5 | |
| History of revascularization | — | 17 | |
| Arteriosclerosis of the aorta | — | 7 | |
| Arteriosclerosis of the kidney | — | 11 | |

TABLE 1-continued

Patient characteristics

| | No cardiovascular events (n = 110) | Symptomatic arteriosclerosis (n = 100) | P-values[#] |
|---|---|---|---|
| Number of organs affected by cardiovascular events | | | |
| 1 | — | 72 | |
| 2 | — | 26 | |
| ≥3 | — | 2 | |

[#]The two patient groups were compared using the Mann-Whitney-U-Test (for numerical data) or the $X^2$-test (for non-numerical data)

TABLE 2

The numerical data selected for the data-based clinical disease profile and the disease activity score

| | | No cardiovascular events (n = 110) | | | | | Symptomatic atherosclerosis (n = 100) | | | | | |
|---|---|---|---|---|---|---|---|---|---|---|---|---|
| Parameter | Method[§] | Maximum value | 75. percentile | Median | 25. Percentile | Minimum value | Maximum value | 75. percentile | Median | 25. percentile | Minimum value | P-value[#] |
| Age (years) | H | 88.0 | 67.75 | 56.0 | 46.25 | 18.0 | 92.0 | 76.0 | 72.0 | 66.75 | 39.0 | <0.001 |
| Smoking (packyears) | H | 150.0 | 25.0 | 1.0 | 0.0 | 0 | 150.0 | 50.0 | 15.0 | 0.0 | 0.0 | 0.018 |
| Number of children | H | 7.0 | 2.0 | 2.0 | 1.0 | 0 | 6.0 | 3.0 | 2.0 | 1.0 | 0.0 | 0.028 |
| Body mass index (kg/m$^2$) | C | 40.1 | 27.75 | 25.6 | 23.25 | 14.5 | 42.40 | 29.73 | 26.4 | 24.07 | 16.59 | 0.085 |
| Waist circumference (cm) | C | 120.0 | 101.0 | 95.0 | 82.0 | 56.0 | 140.0 | 109.0 | 99.5 | 90.0 | 71.0 | 0.006 |
| Hip circumference (cm) | C | 126.0 | 105.0 | 100.0 | 91.0 | 71.0 | 124.0 | 110.0 | 101.5 | 94.0 | 78.0 | 0.078 |
| Waist hip ratio | C | 1.20 | 1.00 | 0.94 | 0.88 | 0.75 | 1.20 | 1.04 | 1.00 | 0.91 | 0.78 | 0.006 |
| Systolic blood pressure left arm supine (mmHg) | C | 180.0 | 140.0 | 130.0 | 110.0 | 85.0 | 195.0 | 160.0 | 140.0 | 120.0 | 90.0 | 0.003 |
| Systolic blood pressure right arm supine (mmHg) | C | 190.0 | 140.0 | 130.0 | 110.0 | 90.0 | 200.0 | 160.0 | 135.0 | 120.0 | 85.0 | 0.005 |
| Systolic blood pressure left arm standing (mmHg) | C | 180.0 | 140.0 | 120.0 | 100.0 | 80.0 | 225.0 | 155.0 | 130.0 | 120.0 | 80.0 | 0.001 |
| Systolic blood pressure right arm standing (mmHg) | C | 200.0 | 140.0 | 120.0 | 110.0 | 80.0 | 190.0 | 150.0 | 130.0 | 120.0 | 80.0 | 0.007 |
| Heart diameter (cm) | X | 17.7 | 14.9 | 13.5 | 12.5 | 9.40 | 19.8 | 16.6 | 15.6 | 13.9 | 11.3 | <0.001 |
| Heart lung ratio | X | 0.61 | 0.49 | 0.47 | 0.43 | 0.35 | 0.71 | 0.56 | 0.51 | 0.48 | 0.38 | <0.001 |
| Ankle brachial index right* | C | 1.46 | 1.24 | 1.14 | 1.06 | 0.76 | 1.50 | 1.15 | 1.00 | 0.95 | 0.42 | <0.001 |
| Ankle brachial index left* | C | 1.45 | 1.21 | 1.15 | 1.07 | 0.70 | 1.50 | 1.13 | 1.02 | 0.86 | 0.43 | <0.001 |
| QT time (sec) | E | 0.50 | 0.40 | 0.37 | 0.35 | 0.27 | 0.55 | 0.43 | 0.40 | 0.37 | 0.21 | <0.001 |
| Peripheral heart rate standing (bpm) | C | 120.0 | 92.0 | 80.0 | 72.0 | 48.0 | 160.0 | 88.0 | 78.0 | 68.0 | 44.0 | 0.02 |
| Creatinin clearance (mL/min per 1.73 m$^2$) | L | 242.2 | 137.1 | 103.8 | 79.5 | 16.91 | 158.1 | 93.3 | 72.4 | 54.6 | 15.2 | <0.001 |
| Glucosuria (negative = 0, + = 1, ++ = 2, +++ = 3) | L | 1.0 | 0.0 | 0.0 | 0.0 | 0.0 | 3.0 | 0.0 | 0.0 | 0.0 | 0.0 | 0.003 |
| Hemoglobin (g/dL) | L | 17.1 | 14.4 | 13.6 | 12.0 | 5.7 | 16.3 | 14.0 | 12.6 | 11.2 | 8.4 | 0.011 |
| Monocytes ($10^9$/L) | L | 3.41 | 0.87 | 0.47 | 0.29 | 0.05 | 2.78 | 0.86 | 0.59 | 0.40 | 0.00 | 0.079 |
| Blood sedimentation rate (mm/h) | L | 105.0 | 27.5 | 10.0 | 4.0 | 2.0 | 114.0 | 31.5 | 13.0 | 6.0 | 1.0 | 0.086 |
| Number of drugs (on admission) | H | 10.0 | 4.0 | 2.0 | 1.0 | 0 | 14.0 | 8.0 | 6.0 | 4.0 | 0.0 | <0.001 |
| Number of medication (current) | O | 11.0 | 5.0 | 4.0 | 2.0 | 0 | 14.0 | 9.0 | 7.0 | 5.0 | 2.0 | <0.001 |
| Number of admissions to this hospital | H | 8.0 | 1.0 | 0.0 | 0.0 | 0 | 15.0 | 3.0 | 1.0 | 0.0 | 0.0 | 0.002 |
| Disease activity score | O | 1.83 | 1.22 | 0.92 | 0.67 | 0.25 | 2.67 | 1.79 | 1.49 | 1.27 | 0.41 | <0.001 |

*Patients (7 without cardiovascular events, 6 with symptomatic atherosclerosis) who had incompressible ankle arteries (=ABI > 1.5) were excluded from this analysis.
[#]The numeric data obtained during the two study periods were compared using Mann-Whitney-U-Test.
[§]Method by which the data was obtained: H = history, C = clinical examination, L = laboratory test, X = chest X-ray, E = electrocardiography, O = others.

Once give the disclosure provided herein, many features, modifications, and improvements will become apparent to the skilled artisan. Such features, modifications, and improvements are therefore considered part of the present invention.

BIBLIOGRAPHY

1. Fuster V, Moreno P R, Fayad Z A, Corti R, Badimon J J. Atherothrombosis and high-risk plaque: part I: evolving concepts. J Am Coll Cardiol 2005; 46(6):937-54.
2. Naghavi M, Libby P, Falk E, Casscells S W, Litovsky S, Rumberger J, et al. From vulnerable plaque to vulnerable patient: a call for new definitions and risk assessment strategies: Part II. Circulation 2003; 108(15):1772-8.
3. Naghavi M, Libby P, Falk E, Casscells S W, Litovsky S, Rumberger J, et al. From vulnerable plaque to vulnerable patient: a call for new definitions and risk assessment strategies: Part I. Circulation 2003; 108(14):1664-72.
4. Assmann G, Cullen P, Schulte H. Simple scoring scheme for calculating the risk of acute coronary events based on the 10-year follow-up of the prospective cardiovascular Munster (PROCAM) study. Circulation 2002; 105(3):310-5.
5. Wilson P W, D'Agostino R B, Levy D, Belanger A M, Silbershatz H, Kannel W B. Prediction of coronary heart disease using risk factor categories. Circulation 1998; 97(18):1837-47.
6. Empana J P, Ducimetiere P, Arveiler D, Ferrieres J, Evans A, Ruidavets J B, et al. Are the Framingham and PROCAM coronary heart disease risk functions applicable to different European populations? The PRIME Study. Eur Heart J 2003; 24(21): 1903-11.
7. Haslam D W, James WP. Obesity. Lancet 2005; 366(9492): 1197-209.
8. Yamada Y, Izawa H, Ichihara S, Takatsu F, Ishihara H, Hirayama H, et al. Prediction of the risk of myocardial infarction from polymorphisms in candidate genes. N Engl J Med 2002; 347(24):1916-23.
9. Bressler R, Bahl J J. Principles of drug therapy for the elderly patient. Mayo Clin Proc 2003; 78(12):1564-77.
10. Ratz Bravo A E, Tchambaz L, Krahenbuhl-Melcher A, Hess L, Schlienger R G, Krahenbuhl S. Prevalence of potentially severe drug-drug interactions in ambulatory patients with dyslipidaemia receiving HMG-CoA reductase inhibitor therapy. Drug Saf 2005; 28(3):263-75.
11. Tinetti M E, Bogardus S T, Jr., Agostini J V. Potential pitfalls of disease-specific guidelines for patients with multiple conditions. N Engl J Med 2004; 351 (27): 2870-4.
12. Kwak B, Mulhaupt F, Myit S, Mach F. Statins as a newly recognized type of immunomodulator. Nat Med 2000; 6(12):1399-402.
13. Jacoby D S, Rader D J. Renin-angiotensin system and atherothrombotic disease: from genes to treatment. Arch Intern Med 2003; 163(10):1155-64.
14. Yusuf S, Hawken S, Ounpuu S, Dans T, Avezum A, Lanas F, et al. Effect of potentially modifiable risk factors associated with myocardial infarction in 52 countries (the INTERHEART study): case-control study. Lancet 2004; 364(9438):937-52.
15. Doobay A V, Anand S S. Sensitivity and specificity of the ankle-brachial index to predict future cardiovascular outcomes: a systematic review. Arterioscler Thromb Vasc Biol 2005; 25(7):1463-9.
16. Fleming C, Whitlock E P, Beil T L, Lederle F A. Screening for abdominal aortic aneurysm: a best-evidence systematic review for the U.S. Preventive Services Task Force. Ann Intern Med 2005; 142(3):203-11.
17. Go A S, Chertow G M, Fan D, McCulloch C E, Hsu C Y. Chronic kidney disease and the risks of death, cardiovascular events, and hospitalization. N Engl J Med 2004; 351(13):1296-305.
18. Third Report of the National Cholesterol Education Program (NCEP) Expert Panel on Detection, Evaluation, and Treatment of High Blood Cholesterol in Adults (Adult Treatment Panel III) final report. Circulation 2002; 106 (25):3143-421.
19. Stoll M, Cowley A W, Jr., Tonellato P J, Greene A S, Kaldunski M L, Roman R J, et al. A genomic-systems biology map for cardiovascular function. Science 2001; 294(5547): 1723-6.
20. Cowley A W, Jr. Genomics and homeostasis. Am J Physiol Regul Integr Comp Physiol 2003; 284(3):R611-27.
21. Van Gaal L F, Vansant G A, De Leeuw I H. Upper body adiposity and the risk for atherosclerosis. J Am Coll Nutr 1989; 8(6):504-14.
22. Clement D L, De Buyzere M L, De Bacquer D A, de Leeuw P W, Duprez D A, Fagard R H, et al. Prognostic value of ambulatory blood-pressure recordings in patients with treated hypertension. N Engl J Med 2003; 348(24): 2407-15.
23. Sukhija R, Aronow W S, Kakar P, Levy J A, Lehrman S G, Babu S. Prevalence of echocardiographic left ventricular hypertrophy in persons with systemic hypertension, coronary artery disease, and peripheral arterial disease and in persons with systemic hypertension, coronary artery disease, and no peripheral arterial disease. Am J Cardiol 2005; 96(6):825-6.
24. Pradhan A D, Manson J E, Rossouw J E, Siscovick D S, Mouton C P, Rifai N. et al. Inflammatory biomarkers, hormone replacement therapy, and incident coronary heart disease: prospective analysis from the Women's Health Initiative observational study. Jama 2002; 288(8):980-7.
25. Dandona P, Aljada A, Chaudhuri A, Mohanty P, Garg R. Metabolic syndrome: a comprehensive perspective based on interactions between obesity, diabetes, and inflammation. Circulation 2005; 111(11):1448-54.
26. Grundy S M. Age as a risk factor: you are as old as your arteries. Am J Cardiol 1999; 83(10):1455-7, A7.

What is claimed is:

1. A method for a data-based clinical disease profile assessment of a disease, the method being embodied in a computer program stored on a non-transitory computer readable storage medium, the computer program being configured to run on a computer processor, the method comprising:

creating, using the computer processor, a database stored on the non-transitory computer readable storage medium comprising a plurality of data records, wherein each data record comprises a number of measurable indicator parameters, wherein the data records are:

either in a first set wherein the data are collected from a first group of individuals having said disease;

or in a second set wherein the data are collected from a second group of individuals without said disease;

the method further comprising:

comparing, by the computer processor, said first set of data with said second set of data for each measurable indicator parameter; and selecting, by the computer processor, a profiling set for said disease activity as a sub record of said measurable indicator parameters including any of said measurable indicator parameters for which the comparison results in a statistically significant difference between data for said measurable indicator parameter from the first set and the second set, wherein the step of selecting comprises using a correlation set, wherein the correlation set is established on the basis of measurable indicator parameters from a relevant number of individuals that forms the basis to correlate members of said collection between measurable indicator parameters irrespective of whether or not statistically significant, using the computer processor, at least two differences of said measurable indicator parameters of the correlation set, wherein the profiling set only comprises parameters having a P-value of less than 0.5 in a statistical test comparing two groups, the statistical test comprising one of a Mann Whitney U test, a student t-test, or a $X^2$ test, when comparison takes place;

using the profiling set and the correlation set to permit personalized and targeted treatment of patients with complex diseases or with a risk of developing the complex diseases and/or to determine trends of a disease within a population, determining, using the computer processor, at least one activity score for at least one disease in a population comprising measuring the measurable indicator parameters of the profiling set for said population and determining said activity score of said disease in said population from an average of the sum of said profiling set, wherein said at least activity score is established in said population over time in predetermined time intervals to assess changes in said population for said disease over time.

2. The method according to claim 1, comprising calculating, using the computer processor, the percentile distribution of each measurable indicator parameter of said profiling set for representation as color, shade or value coding reflecting the percentile distribution.

3. The method according to claim 2, wherein said coding is based on percentile ranges such as fertile, quartile, quintile, sextile, septile, octile or nonile ranges of said percentile distribution.

4. The method according to claims 2, wherein said first group serves as a standard reference.

5. The method according to claim 1, wherein the upper boundary of the P-value is taken from the group comprising 0.4, 0.3, 0.2, 0.1, 0.05, 0.025, 0.01, 0.005, 0.0025 and 0.001.

6. The method according to claim 1, wherein selecting data sets from the first set and the second set for the sub record of said measurable indicator parameters is restricted to data sets which were collected approximately within the last 5 years, 4 years, 3 years, 2 years, 1 year, 9 months, 6 months, 3 months, 2 months, 1 months, 2 weeks, 1 week, 5 days, 2 days or 24 hours.

7. The method according to claim 1, wherein a population is defined encompassing predefined groups of individuals, wherein the step of selecting data sets from the first set and the second set for the sub record of said measurable indicator parameters is restricted to data sets wherein the groups of individuals of the two groups stem from a population.

8. The method of claim 1, wherein the predetermined time intervals are chosen from the group comprising every 3 month, every six month, every year or every other year.

9. The method of claim 1, further comprising correlating, using the computer processor, the changes within said at least one activity score to environmental difference between points in time at which said at least one activity score is established.

10. The method according to claim 1, further comprising correlating, using the computer processor, said measurable indicator parameters of a correlation set; and determining positive and/or negative correlations between different of said indicator parameters.

11. The method according to claim 1, wherein said condition and/or disease is arteriosclerosis, chronic obstructive pulmonary disease, asthma, severe bacterial infections including pneumonia, sepsis, meningitis, endocarditis, and acute or chronic viral infections, osteoporosis, an autoimmune disease, osteoarthrosis, heart failure, drug dependency, alcoholism, an allergy, cancer, diabetes mellitus Type 2 and metabolic syndrome, arterial hypertension, obesity, smoking, venous thrombosis or pulmonary embolism.

12. The method according to claim 1, wherein the measurable indicator parameters of the profiling set are selected from a group comprising myocardial infarction, significant stenosis of coronary arteries as assessed by angiography, angina pectoris with signs of myocardial ischemia, history of coronary bypass surgery, ischemic stroke, history of carotid surgery, ankle brachial index <0.9, symptoms of claudicatio intermittens, significant stenosis of arteries and symptoms of claudicatio, history of peripheral bypass surgery, symptomatic aortic aneurysm, infrarenal diameter >3 cm, renal artery stenosis, impaired renal function with normal urine analysis, history of renal artery revascularization procedures, male sex, arterial hypertension, diabetes mellitus, dyslipidemia, smoking and positive family history for cardiovascular disease.

* * * * *